US009783635B2

(12) United States Patent
Schubert et al.

(10) Patent No.: US 9,783,635 B2
(45) Date of Patent: Oct. 10, 2017

(54) POLYOXYALKYLENES WITH PENDANT LONG-CHAIN ACYLOXY GROUPS AND METHOD FOR PRODUCING SAME USING DMC CATALYSTS

(71) Applicants: Frank Schubert, Neukirchen-Vluyn (DE); Wilfried Knott, Essen (DE)

(72) Inventors: Frank Schubert, Neukirchen-Vluyn (DE); Wilfried Knott, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/888,872

(22) PCT Filed: Apr. 10, 2014

(86) PCT No.: PCT/EP2014/057238
§ 371 (c)(1),
(2) Date: Nov. 3, 2015

(87) PCT Pub. No.: WO2014/180622
PCT Pub. Date: Nov. 13, 2014

(65) Prior Publication Data
US 2016/0053051 A1 Feb. 25, 2016

(30) Foreign Application Priority Data
May 7, 2013 (DE) ........................ 10 2013 208 328

(51) Int. Cl.
| C07C 69/66 | (2006.01) |
| C08G 65/332 | (2006.01) |
| C08G 65/24 | (2006.01) |
| C08G 65/26 | (2006.01) |
| C08L 71/03 | (2006.01) |
| C07C 69/708 | (2006.01) |

(52) U.S. Cl.
CPC ........ *C08G 65/3322* (2013.01); *C07C 69/708* (2013.01); *C08G 65/24* (2013.01); *C08G 65/2663* (2013.01); *C08G 65/332* (2013.01); *C08L 71/03* (2013.01)

(58) Field of Classification Search
USPC ........................................................ 560/186
See application file for complete search history.

(56) References Cited

U.S. PATENT DOCUMENTS

| 3,285,870 | A | 11/1966 | Vandenberg |
| 4,092,339 | A * | 5/1978 | Stevens ................. C08L 71/02 554/116 |
| 5,371,161 | A | 12/1994 | Knott |
| 5,475,127 | A | 12/1995 | Klein et al. |
| 5,777,013 | A | 7/1998 | Gardiner et al. |
| 5,934,579 | A | 8/1999 | Hiersche et al. |
| 5,981,812 | A | 11/1999 | Eufinger et al. |
| 6,291,622 | B1 | 9/2001 | Droese et al. |
| 6,307,082 | B1 | 10/2001 | Klein et al. |
| 6,858,663 | B2 | 2/2005 | Knott et al. |
| 7,018,458 | B2 | 3/2006 | Knott et al. |
| 7,125,585 | B2 | 10/2006 | Dudzik et al. |
| 7,157,541 | B2 | 1/2007 | Knott et al. |
| 7,196,153 | B2 | 3/2007 | Burkhart et al. |
| 7,598,334 | B2 | 10/2009 | Ferenz et al. |
| 7,612,158 | B2 | 11/2009 | Burkhart et al. |
| 7,612,159 | B2 | 11/2009 | Burkhart et al. |
| 7,619,035 | B2 | 11/2009 | Henning et al. |
| 7,645,848 | B2 | 1/2010 | Knott et al. |
| 7,754,778 | B2 | 7/2010 | Knott et al. |
| 7,825,205 | B2 | 11/2010 | Knott et al. |
| 7,825,206 | B2 | 11/2010 | Neumann et al. |
| 7,825,209 | B2 | 11/2010 | Knott et al. |
| 8,138,294 | B2 | 3/2012 | Henning et al. |
| 8,247,525 | B2 | 8/2012 | Schubert et al. |
| 8,268,939 | B2 | 9/2012 | Ebbrecht et al. |
| 8,283,422 | B2 | 10/2012 | Schubert et al. |
| 8,309,664 | B2 | 11/2012 | Knott et al. |
| 8,309,673 | B2 | 11/2012 | Schubert et al. |
| 8,324,325 | B2 | 12/2012 | Knott et al. |
| 8,334,355 | B2 | 12/2012 | Henning et al. |
| 8,349,907 | B2 | 1/2013 | Henning et al. |
| 8,420,748 | B2 | 4/2013 | Henning et al. |
| 8,450,514 | B2 | 5/2013 | Schubert et al. |
| 8,455,603 | B2 | 6/2013 | Ferenz et al. |
| 8,557,944 | B2 | 10/2013 | Henning et al. |
| 8,598,295 | B2 | 12/2013 | Henning et al. |
| 8,609,798 | B2 | 12/2013 | Knott et al. |
| 8,623,984 | B2 | 1/2014 | Henning et al. |

(Continued)

FOREIGN PATENT DOCUMENTS

| CN | 1702093 A | 11/2005 |
| CN | 101376707 A | 3/2009 |

(Continued)

OTHER PUBLICATIONS

Combined Chinese Office Action and Search Report dated Jul. 6, 2016 in Patent Application No. 201480025679.8 (with English translation of categories of cited documents).
"The combined polymerization of epoxyethane and expoxy propane", Chemical industry publishing house, 2003, pp. 684-686 and Cover Pages.
"Polyether polyhydric alcohol initiator", Hand book of raw materials and additives for polyurethanes, Chemical industry publishing house, 2013, pp. 189-191 and Cover Pages.
"The polyether polyhydric alcohol", 2003, A Handbook of Usual Crude Material for Fine Chemical Industry, Golden Shield publishing house, 2003, pp. 446-447 and Cover Page.
Reina Jose A., et al. "Crosslinkable epichlorohydrin terpolymers with aromatic pendant groups", Macromolecular Chemistry and Physics, vol. 198, No. 2, Feb. 1, 1997, pp. 581-595, XP000684249.
International Search Report dated Sep. 30, 2014 for PCT/EP2014/057238 filed on Apr. 10, 2014.

*Primary Examiner* — Sudhakar Katakam
*Assistant Examiner* — Ana Z Muresan
(74) *Attorney, Agent, or Firm* — Oblon, McClelland, Maier & Neustadt, L.L.P.

(57) ABSTRACT

The invention relates to polyoxyalkylenes having pendant long-chain acyloxy radicals and to a process for preparation thereof by an alkoxylation reaction using double metal cyanide (DMC) catalysts.

8 Claims, No Drawings

(56) References Cited

U.S. PATENT DOCUMENTS

| | | |
|---|---|---|
| 8,722,834 B2 | 5/2014 | Knott et al. |
| 8,722,836 B2 | 5/2014 | Knott et al. |
| 8,729,207 B2 | 5/2014 | Hartung et al. |
| 8,772,423 B2 | 7/2014 | De Gans et al. |
| 8,779,079 B2 | 7/2014 | Henning et al. |
| 8,802,744 B2 | 8/2014 | Knott et al. |
| 8,841,400 B2 | 9/2014 | Henning et al. |
| 8,883,932 B2 | 11/2014 | Brugger et al. |
| 8,921,437 B2 | 12/2014 | Knott et al. |
| 8,946,369 B2 | 2/2015 | Henning et al. |
| 8,957,009 B2 | 2/2015 | Schubert et al. |
| 8,969,502 B2 | 3/2015 | Knott et al. |
| 8,974,627 B2 | 3/2015 | Schubert et al. |
| 8,993,706 B2 | 3/2015 | Schubert et al. |
| 9,035,011 B2 | 5/2015 | Ferenz et al. |
| 9,051,424 B2 | 6/2015 | Lobert et al. |
| 9,068,044 B2 | 6/2015 | Schubert et al. |
| 2007/0128143 A1 | 6/2007 | Gruning et al. |
| 2007/0299242 A1* | 12/2007 | Faecke ............... C08G 65/06 528/415 |
| 2009/0137752 A1 | 5/2009 | Knott et al. |
| 2010/0022435 A1 | 1/2010 | Henning et al. |
| 2010/0081781 A1 | 4/2010 | Schubert et al. |
| 2010/0266518 A1 | 10/2010 | Springer et al. |
| 2011/0046305 A1 | 2/2011 | Schubert et al. |
| 2011/0160342 A1 | 6/2011 | Matoba et al. |
| 2011/0230619 A1 | 9/2011 | Kuppert et al. |
| 2011/0301254 A1 | 12/2011 | Knott et al. |
| 2012/0028022 A1 | 2/2012 | Brugger et al. |
| 2012/0037036 A1 | 2/2012 | Veit et al. |
| 2012/0068110 A1 | 3/2012 | Schubert et al. |
| 2012/0190760 A1 | 7/2012 | Henning et al. |
| 2012/0282210 A1 | 11/2012 | Henning et al. |
| 2013/0041102 A1 | 2/2013 | Albrecht et al. |
| 2013/0041115 A1 | 2/2013 | Knott et al. |
| 2013/0213267 A1 | 8/2013 | Fiedel et al. |
| 2013/0245304 A1 | 9/2013 | Schubert et al. |
| 2013/0345318 A1 | 12/2013 | Schubert et al. |
| 2014/0256844 A1 | 9/2014 | Henning et al. |
| 2014/0303065 A1 | 10/2014 | Jazkewitsch et al. |
| 2014/0309446 A1 | 10/2014 | Amajjahe et al. |
| 2015/0004112 A1 | 1/2015 | Ritter et al. |
| 2015/0004113 A1 | 1/2015 | Ritter et al. |
| 2015/0023900 A1 | 1/2015 | Knott et al. |
| 2015/0057369 A1 | 2/2015 | Ferenz et al. |
| 2015/0057412 A1 | 2/2015 | Knott et al. |
| 2015/0080593 A1 | 3/2015 | Henning et al. |

FOREIGN PATENT DOCUMENTS

| | | |
|---|---|---|
| CN | 102131870 A | 7/2011 |
| CN | 102656209 A | 9/2012 |
| CN | 102786678 A | 11/2012 |
| EP | 2 316 884 A1 | 5/2011 |
| JP | 2009-062448 A | 3/2009 |

* cited by examiner

POLYOXYALKYLENES WITH PENDANT LONG-CHAIN ACYLOXY GROUPS AND METHOD FOR PRODUCING SAME USING DMC CATALYSTS

The invention relates to polyoxyalkylenes having pendant long-chain acyloxy radicals and to a process for preparation thereof by an alkoxylation reaction using double metal cyanide (DMC) catalysts.

The polyoxyalkylenes having pendant acyloxy radicals that are of interest here are especially polyether alcohols, often also referred to as polyethers or polyetherols for short. Polyethers or polyetherols as such have been known for some time and are produced in large volumes. Among other applications, they serve, through reaction with polyisocyanates, as starting compounds for producing polyurethanes, or else for production of surfactants.

Typically, a hydroxy-functional starter such as butanol, allyl alcohol, propylene glycol or glycerol is reacted in the presence of a suitable catalyst with alkylene oxides such as ethylene oxide, propylene oxide or butylene oxide in an alkoxylation reaction to give an alkoxylation product or polyether. Most processes for preparing such alkoxylation products make use of basic catalysts, for example the alkali metal hydroxides and the alkali metal methoxides. The use of KOH is particularly widely used. However, alkaline catalysis is not always employable, for example in the presence of base-labile functional groups in the reactants. For example, the alkoxylation of epihalohydrins using alkali metal hydroxides or alkali metal methoxides is impracticable.

Therefore, processes for acidic catalysis with $HBF_4$ and Lewis acids, for example $BF_3$, $AlCl_3$ and $SnCl_4$, in the alkoxylation have been developed, for example in DE 10 2004 007561 (US 2007 185353). A disadvantage in acid-catalysed polyether synthesis is the inadequate regioselectivity in the ring opening of unsymmetric oxiranes, for example propylene oxide and epichlorohydrin, the effect of which is that polyoxyalkylene chains having some secondary and some primary OH termini are obtained in an uncontrollable manner. Moreover, the achievable molar masses of the polyethers compared to other catalysts are relatively low as a result of chain terminations and side reactions.

Catalysts used in the last few years for preparation of polyethers have increasingly been double metal cyanide (DMC) catalysts. The DMC-catalysed alkoxylation proceeds very selectively and rapidly and permits the preparation of polyethers having high molar masses and comparatively low polydispersity. The preparation and use of double metal cyanide complexes as alkoxylation catalysts has been known since the 1960s and is outlined in U.S. Pat. Nos. 3,427,256, 3,427,334, 3,427,335, 3,278,457, 3,278,458 and 3,278,459 for example. Among the ever more effective types of DMC catalysts developed further in the subsequent years and described in U.S. Pat. Nos. 5,470,813 and 5,482,908, for example, a special position is occupied by zinc-cobalt-hexacyano complexes. Because of their exceptionally high activity, only low catalyst concentrations are required for preparation of polyethers.

Polyethers which are prepared proceeding from an OH-functional starter are widely used. The polyethers obtained therefrom in turn have terminal OH groups. For example, when butanol, hexanediol or glycerol is used, polyethers having one, having two or having three chain-terminal hydroxyl groups are formed.

The prior art includes various documents in which fatty alcohols, fatty acids or fatty amines are used as starter compounds for the alkoxylation reaction. A good overview is given by "N. Schonfeldt, Surface Active Ethylene Oxide Adducts, Pergamon Press, 1969". Polyethers derived from fatty alcohols, fatty amines or fatty acids are typically linear chains, one end of which is formed by the hydrophobic hydrocarbyl unit having usually 8 to 22 carbon atoms. Thus, typically only one hydrophobic moiety is present per molecule.

In addition, the person skilled in the art is aware of polyethers which are prepared after the alkoxylation by an esterification of the terminal OH groups with carboxylic acids, for example fatty acids. Polyethylene glycols or polypropylene glycols are thus converted to the corresponding esters in a further reaction with elimination of water. The esterification may take place at one or both OH groups according to the stoichiometry. Frequently, products thus obtained are mixtures of mono- and diesterified compounds. The number of hydrophobic units obtainable in this way per surfactant molecule is limited by the number of OH functions in the starting material.

More highly esterified polyethers are obtained according to the prior art when the starter compounds used for the alkoxylation reaction are polyols such as polyglycerol, sorbitol or, for example, sucrose. A common factor in all the aforementioned structures is that the hydrophobic moieties introduced by esterification are always arranged in terminal positions in relation to the polyether main chain and side chain, but never in pendant positions in the middle of either.

The use of glycidyl esters as monomer in the alkoxylation reaction is an attempt made in the prior art to get round the aforementioned structural restriction. For instance, JP 2009062448 describes the copolymerization of C1-C6 alkyl glycidyl esters with ethylene oxide and allyl glycidyl ethers to give vulcanizable polymers. DE 1250421 describes the Lewis acid-catalysed alkoxylation of C16-C30 fatty acid glycidyl esters to give waxy polymers that are solid at room temperature and find use as a constituent of polishes in automotive care and furniture care. The process disclosed in U.S. Pat. No. 3,285,870 describes the preparation of copolymers from unsaturated glycidyl esters such as glycidyl methacrylate and epichlorohydrin in the presence of triethylaluminium as catalyst. Terpolymers of octyl glycidyl esters, propylene oxide and carbon dioxide are obtainable by the route described by Yan-Hua Jiang et al. in Yingyong Huaxue (2009), 26 (7), 770ff., with the aid of specific catalysts from the group of the rare earth complexes. A fundamental disadvantage of all processes that use glycidyl esters is the lability thereof under the action of basic or acidic alkoxylation catalysts. Under the usually highly acidic or highly alkaline conditions of an alkoxylation reaction catalysed, for example, with KOH or alkali metal methoxide, ester hydrolyses take place, and so pendant OH groups form on the polyether chain, which are in turn a starting point for further alkoxylation reactions and which ultimately lead to branched reaction products having reduced ester functionality. A further disadvantage is the lack of commercial availability of fatty acid glycidyl esters, since they are preparable with difficulty in pure form from fatty acids and epichlorohydrin because of the hydrolysis-sensitive ester group thereof.

Several processes describe the synthesis of polyethers esterified in pendant positions using polyepichlorohydrin and epichlorohydrin-ethylene oxide copolymers. For example, A. Kameyama in Polymer Journal Vol. 28, No 2. 155-158 (1996) describes the partial substitution of Cl in polyepichlorohydrin in a reaction with benzoic acid in the presence of 1,8-diazabicyclo[5.4.0]undec-7-ene (DBU) and aprotic solvents. It is a feature of the reaction products that they contain, as well as residual [—$CH_2$—$CH(CH_2Cl)$—O—] units, benzoic ester units of the [—$CH_2$—$CH(CH_2OC(=O)C_6H_5)$—O—] type. J. C. Ronda uses, as detailed in J. Polym. Sci. Part A, Polym. Chem. Vol. 42, 326-340 (2004), alkali metal salts of aromatic carboxylic acids, in order to esterify polyepichlorohydrin in pendant positions with partial Cl substitution. The modified polyepichlorohydrins having aromatic ester groups as thus obtained feature liquid-crystalline properties. The reaction of aromatic carboxylic acids with polyepichlorohydrin or epichlorohydrin-ethylene oxide copolymers with partial Cl substitution is described by J. A. Reina in Macromol. Chem. Phys. 198, 581-595 (1997).

A common factor in these processes is that they are restricted to polyepichlorohydrin of high molar masses (solids) and high molecular weight epichlorohydrin-ethylene oxide copolymers (solids). Moreover, only partial substitution of Cl takes place with formation of acyloxy groups. The products obtained, because of their chemical structure, are not surfactants but highly chlorinated polymeric materials.

Halogen-substituted polyethers which are obtained using DMC catalysts and epihalohydrins are known from the document U.S. Pat. No. 7,423,112. The halogenated polyethers described therein are converted to amine-functional polyethers in a further reaction with amines in the manner of a substitution reaction.

Catalysts used for the polyaddition of epichlorohydrin are also $BF_3$, $SnCl_4$ and $SbCl_5$. A disadvantage is that only polymers having low molar masses are obtainable in this way.

The problem addressed by the present invention was that of providing novel alkoxylation products bearing pendant ester groups, which do not have at least one disadvantage of the prior art, and a process for preparation thereof.

The problem is solved by alkoxylation products having long-chain pendant acyloxy radicals as detailed in the claims, preparable in a process which at least partly converts pendant chloromethyl groups in the corresponding polyoxyalkylenes directly to methylene groups bearing long-chain acyloxy radicals.

The present invention therefore provides polyoxyalkylenes having pendant long-chain acyloxy radicals having at least the structural unit [—$CH_2$—$CH(CH_2O(acyl\ radical))$—O—] and the structural unit [—$CH_2$—$CH(CH_3)$—O—].

One advantage of the inventive compounds is that they do not have any methylidene groups.

A further advantage of the inventive compounds is that they are free of pendant hydroxymethyl groups.

A further advantage of the inventive compounds can be that they do not have any halogen atoms, especially any chlorine atoms.

The present invention further provides a process for preparing the inventive polyoxyalkylenes having pendant long-chain acyloxy radicals, comprising a first step (i) in which a starter compound is reacted catalytically with epoxides, the epoxides comprising at least epichlorohydrin and propylene oxide, a second step (ii) in which chloromethyl groups are reacted with long-chain carboxylates to give long-chain acyloxy radicals, optionally a third step (iii) in which the reaction mixture is neutralized and the resultant salts are removed, and solvents can optionally also be removed in the third step (iii).

One advantage of the process according to the invention is that the chloromethyl groups are not hydrolysed to the hydroxymethyl group. Thus, the product of the process is free of pendant hydroxymethyl groups.

A further advantage of the process according to the invention is that the second step (ii) does not lead to elimination. Thus, the product of the process is free of methylidene groups.

A further advantage of the process according to the invention is that it gives access to polyoxyalkylenes having pendant long-chain acyloxy radicals of great structural variety.

The process according to the invention is particularly economically viable since there is no need to prepare complicated epoxides having long-chain acyloxy radicals.

The present invention likewise provides for the use of the inventive polyoxyalkylenes having pendant long-chain acyloxy radicals as interface-active polymers.

The invention thus provides polyoxyalkylenes having pendant long-chain acyloxy radicals having at least the structural unit [—$CH_2$—$CH(CH_2O(acyl\ radical))$—O—] and the structural unit [—$CH_2$—$CH(CH_3)$—O—].

It is a feature of the inventive polyoxyalkylenes having pendant long-chain acyloxy radicals that they satisfy the formula (I)

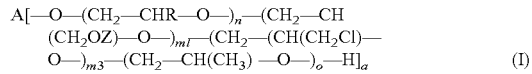

$$A[—O—(CH_2—CHR—O—)_n—(CH_2—CH(CH_2OZ)—O—)_{m1}—(CH_2—(CH(CH_2Cl)—O—)_{m3}—(CH_2—CH(CH_3)—O—)_o—H]_a \quad (I)$$

where
A is either hydrogen or an organic radical of an organic starter compound and, in this case, is a radical having at least one carbon atom,
R is independently hydrogen, an alkyl group having 2-18 carbon atoms or an aromatic radical, the aromatic radical preferably being a phenyl radical,
Z is the radical of an organic acid of the formula —C(=O)—$Z_E$ where $Z_E$ is an organic radical, preferably a linear or branched, saturated or unsaturated aliphatic hydrocarbyl radical having 7 to 22 carbon atoms or an aromatic hydrocarbyl radical having 6 to 21 carbon atoms, most preferably having 6 to 17 carbon atoms,
$m_1$ is 1 up to 50, preferably greater than 1 up to 30, more preferably 2 up to 20,
$m_3$ is 0 up to 10, preferably 0 up to 6, more preferably greater than 0 up to 4, especially less than 2,
n is 0 up to 200, preferably 0 up to 150, more preferably 0 up to 100.
o is 1 up to 1000, preferably 5 up to 800, further preferably 8 up to 500 and more preferably 10 up to 400.
a is 1 up to 8 preferably greater than 1 up to 6, more preferably 1, 2, 3 or 4.

The Z radical thus corresponds to the acyl radical. Together with the oxygen atom, the OZ group forms the acyloxy radicals claimed.

The R radical is preferably H, ethyl or phenyl, preferably exclusively H.

The inventive polyoxyalkylenes having pendant long-chain acyloxy radicals have a weight-average molar mass of 400 to 50 000 g/mol, preferably of 800 to 35 000 g/mol and more preferably of 1200 to 25 000 g/mol.

Pure epichlorohydrin homopolymer (polyepichlorohydrin) is not used as precursor for the inventive polyoxyalkylenes having pendant long-chain acyloxy radicals. The index o is therefore always equal to or greater than 1.

The organic A radical is preferably a radical of the compound of the formula (II) described in the process:

$$A[\text{---}OH]_a \quad (II)$$

A is thus the a-valent radical of an organic compound.

Preferred A radicals are those which derive from compounds of the group of the mono- or polyhydric monomeric alcohols, where the alcohols may also be oligomeric or polymeric; the alcohols also include phenols and carbohydrate derivatives. Particular preference is given to the radicals which derive from allyl alcohol, butanol, octanol, dodecanol, stearyl alcohol, 2-ethylhexanol, cyclohexanol, benzyl alcohol, ethylene glycol, propylene glycol, di-, tri- and polyethylene glycol, 1,2-propylene glycol, di- and polypropylene glycol, butane-1,4-diol, hexane-1,6-diol, trimethylolpropane, glycerol, pentaerythritol, sorbitol or hydroxyl group-bearing compounds based on natural products.

The A radicals preferably have a molar mass of 15 to 4983 g/mol, especially 83 to 3983 g/mol. In the case of polymeric A radicals, the preferred molar masses are understood to mean weight-average molar masses.

If a plurality of starter compounds have been used as a mixture, the index a may also be subject to a statistical distribution.

The molar mass Mw of the inventive polyoxyalkylenes having pendant long-chain acyloxy radicals is variable over wide ranges. Preferably, the molar mass Mw is from 400 to 50 000 g/mol, preferably from 800 to 35 000 g/mol and more preferably from 1200 to 25 000 g/mol.

The acyloxy radicals of the inventive polyoxyalkylenes are radicals of organic acids as described in the process according to the invention.

The inventive polyoxyalkylenes having pendant long-chain acyloxy radicals, or those prepared in accordance with the invention, are preferably colourless to yellow-orange products which may be clear or opaque. According to the structure of the polyoxyalkylene chain and the ester functionality, the products are liquid, waxy or solid at room temperature. The inventive polyoxyalkylenes having pendant long-chain carboxylate radicals which are rich in oxyethylene groups and/or wherein the $Z_E$ radicals have long-chain saturated alkyl groups have the advantage that they are usually waxy or solid, and in some cases crystalline. In contrast, those products having a low oxyethylene group content and/or in which the $S_E$ radicals are branched aliphatic or unsaturated aliphatic hydrocarbyl radicals have the advantage of usually being liquid.

Preferably, the inventive polyoxyalkylenes having pendant long-chain acyloxy radicals do not have any halogen atoms, especially any chlorine atoms. More preferably, the inventive polyoxyalkylenes do not have any terminal chloromethyl groups.

Further preferably, the inventive polyoxyalkylenes having pendant long-chain acyloxy radicals do not have any terminal structural unit with a long-chain acyloxy radical.

Especially preferably, the inventive polyoxyalkylenes having pendant long-chain acyloxy radicals do not have any chloromethyl groups or any double bonds, especially any methylidene groups ($=CH_2$).

The absence of methylidene groups in the inventive polyoxyalkylenes having pendant long-chain acyloxy radicals has the advantage that there is no possibility of side reactions at these methylidene groups. The person skilled in the art is aware of such side reactions, one example being oxidation reactions, for example by oxygen, and polymerizations or crosslinkings.

The indices shown here and the ranges of values for the indices given may be understood as average values of the possible statistical distribution of the structures and/or mixtures thereof that are actually present. This also applies to structural formulae reproduced exactly per se as such, as for example to formulae (I), (II) and (III).

The units referred to by n, $m_1$, $m_3$ and o may either be in a statistical mixture or else may be present in blocks in the chain.

The indices m1, m2, m3, a, n, o shown in formulae (I), (II) and (III) and the ranges of values for the indices given are understood to mean the average values of the possible statistical distribution of the structures actually present and/or mixtures thereof. This also applies to structural formulae exactly reproduced per se as such.

The modes of detection of freedom from halogen in accordance with the invention and the absence of methylidene groups are familiar to those skilled in the art. Within the scope of the present invention, halogen-free and free of methylidene groups are understood to mean that the corresponding resonance signals are undetectable in the $^{13}C$ NMR spectra. The person skilled in the art is aware of the position and multiplicity of the signals; more particularly, the signals of the methylidene groups in the $^{13}C$ NMR can be assigned reliably.

Statistical distributions may have a block structure with any number of blocks and any sequence or may be subject to a randomized distribution; they may also have an alternating structure or else form a gradient along the chain; more particularly, they may also form any mixed forms thereof where, as the case may be, groups of different distributions may follow on from one another. Specific executions may lead to restrictions in the statistical distributions as a result of the execution. For all ranges which are not affected by the restriction, there is no change in the statistical distribution.

The inventive polyoxyalkylenes having pendant long-chain carboxylate radicals can be prepared by the processes known in the prior art; they are preferably prepared by the process according to the invention which follows.

The process according to the invention comprises a first step (i) in which a starter compound is reacted catalytically with epoxides, the epoxides comprising at least epichlorohydrin and propylene oxide, a second step (ii) in which chloromethyl groups are reacted with long-chain carboxylates to give long-chain acyloxy radicals, optionally a third step (iii) in which the reaction mixture is neutralized and the resultant salts are removed, and solvents can optionally also be removed in the third step (iii).

The process according to the invention for preparing the inventive polyoxyalkylenes having pendant long-chain acyloxy radicals comprises the following process steps:

In the first step (i),
a) one or more compounds of the formula (II)

$$A[\text{---}OH]_a \quad (II)$$

where the A radical and the index a are each as defined above are reacted with
b) epichlorohydrin and propylene oxide and optionally one or more further alkylene oxides having 2 to 18 carbon atoms and any desired mixtures thereof in the presence of
c) a double metal cyanide catalyst, in an alkoxylation reaction.

In the second step (ii), the reaction products from the first step (i)
a) are reacted with one or more carboxylate compounds or any desired mixtures thereof,
b) optionally in the presence of solvents,
c) optionally in the presence of one or more phase transfer catalysts, at a temperature of 60 to 300° C.

In the optional third step (iii), the reaction products from the second step (ii)
a) are optionally neutralized with an inorganic or organic acid,
b) solvents are optionally distilled off,
c) any salts formed are removed, preferably by filtration or by phase separation.

First Step (i):

Starter compounds used for the alkoxylation reaction may be any compounds of the formula (II)

$$A[-OH]_a \qquad (II)$$

The compounds of the formula (II) have at least one hydroxyl group and A=hydrogen or organic radical. The organic radical has at least one carbon atom. In the context of the present invention, starter compounds are understood to mean substances that form the beginning (start) of the polyether or alkoxylation product to be prepared, which is obtained by addition of alkylene oxides. The starter compound is preferably selected from the group of the alcohols, polyetherols and phenols. The starter compound containing the A group used is preferably a mono- or polyfunctional polyether alcohol and/or a mono- or polyfunctional alcohol, or any desired mixtures thereof.

OH-functional starter compounds of the formula (II) used are preferably compounds having molar masses of 32 to 5000 g/mol, especially 100 to 4000 g/mol. These starters have 1 to 8 and preferably 1 to 4 hydroxyl groups. Examples include allyl alcohol, butanol, octanol, dodecanol, stearyl alcohol, 2-ethylhexanol, cyclohexanol, benzyl alcohol, ethylene glycol, propylene glycol, di-, tri- and polyethylene glycol, 1,2-propylene glycol, di- and polypropylene glycol, butane-1,4-diol, hexane-1,6-diol, trimethylolpropane, glycerol, pentaerythritol, sorbitol or hydroxyl group-bearing compounds based on natural products.

Where reference is made within the scope of this invention to natural products, for example sorbitol, what is meant is basically all the isomers, preferably the isomers which occur naturally in each case, and thus in the present case therefore D-(-)-sorbitol. Natural products are defined by reference to the scope of the "Dictionary of Natural Products", Chapman and Hall/CRC Press, Taylor and Francis Group, e.g. in the online version from 2011: http://dnp.chemnetbase.com/.

Starter compounds used are preferably low molecular weight polyetherols having 1 to 8 hydroxyl groups and weight-average molar masses of 100 to 5000 g/mol, which have preferably been prepared in turn beforehand by DMC-catalysed alkoxylation. Particularly suitable are polypropylene glycols, polyethylene glycols, poly(ethylene-co-propylene) glycols, polybutylene glycols, poly(propylene-co-butylene) glycols, poly(butylene-co-ethylene) glycols, comprising at least one OH group. Of these polyalkylene glycols, advantageous compounds are especially those which derive from butanol, allyl alcohol, octanol, decanol, dodecanol, butanediol, hexanediol and glycerol.

It is thus possible to use the products of the first step (i) of the process according to the invention as starter compounds again in the process according to the invention if higher molar masses are to be achieved. The usable starters also include halogenated compounds, including polyetherols that derive from epichlorohydrin. In the second step (ii) of the process according to the invention, the halogens bonded to the starter may also be converted to pendant ester groups.

As well as aliphatic and cycloaliphatic compounds having OH groups, suitable compounds of the formula (II) also include any desired compounds having 1 to 8 phenolic OH functions. These include, for example, phenol, alkyl- and arylphenols, bisphenol A and novolacs.

In the first step (i) of the process according to the invention for preparing the chlorinated alkoxylation products, as well as epichlorohydrin, propylene oxide is always used. In addition, it is possible to use further epoxide compounds, especially alkylene oxides having 2 to 18 carbon atoms, preferably ethylene oxide, 1,2-butylene oxide and styrene oxide.

The different monomers may be used in pure form or as a mixture. It is also possible to meter a further epoxide into an epoxide already present in the reaction mixture continuously over time, so as to give rise to an increasing concentration gradient of the epoxide added continuously. The polyoxyalkylenes formed are thus subject to a statistical distribution in the end product. In this case, restrictions may be determined by the metered addition. In this present case of continuous addition of a further epoxide to an epoxide already present in the reaction mixture, a structure gradient along the length of the chain is then to be expected. The correlations between metered addition and product structure are known to those skilled in the art.

The molar ratio of epichlorohydrin relative to the OH groups of the starter compounds is preferably from 50:1 to 1:1, preferably from 40:1 to 2:1, more preferably from 25:1 to 3:1.

The molar ratio of epichlorohydrin to the other alkylene oxides is variable within wide limits and is preferably from 1:1000 to 1:0.1, more preferably from 1:200 to 1:0.5, especially preferably from 1:100 to 1:1.5.

The structural units of the formula (I) referred to by the indices n and o are thus preferably in a molar excess based on the monomer unit which derives from epichlorohydrin and is referred to by the index $m_1$.

DMC catalysts used in the alkoxylation reaction may be any known DMC catalysts, preferably those which include zinc and cobalt, more preferably those which include zinc hexacyanocobaltate(III). Preference is given to using the DMC catalysts described in U.S. Pat. No. 5,158,922, US 2003 0119663, WO 01/80994 or in the documents cited above. The catalysts may be amorphous or crystalline.

In the reaction mixture for the first step (i), the catalyst concentration is preferably greater than 0 up to 2000 ppmw (ppm by mass), preferably 30 to 1500 ppmw, based on the total mass of the reaction mixture. The catalyst is preferably metered into the reactor only once. The amount of catalyst should preferably be set so as to give sufficient catalytic activity for the process. The catalyst may be metered in solid form or in the form of a catalyst suspension.

In order to start the DMC-catalysed reaction, it may be advantageous first to activate the catalyst with a portion of alkylene oxide, preferably with propylene oxide. After the alkoxylation reaction has set in, it is possible to commence the epichlorohydrin/alkylene oxide copolymerization. According to the target structure, the addition of epichlorohydrin/alkylene oxide may be interrupted once or more than once by addition of exclusively alkylene oxide. It is especially preferable, after the metered addition of epichlorohydrin/alkylene oxide has ended, to add further alkylene oxide, preferably propylene oxide or ethylene oxide.

The reaction temperature in the first step (i) is preferably 60 to 250° C., more preferably 90 to 160° C. and especially preferably 100 to 130° C.

The pressure in the first step (i) is preferably 0.02 bar to 100 bar, preferably 0.05 bar to 20 bar (absolute).

More preferably, the first step (i) of the process according to the invention is conducted at a temperature of 100 to 130° C. and a pressure of from 0.05 to 20 bar.

The reaction in the first step (i) can be conducted in an inert solvent, for example for the purpose of lowering the viscosity.

After the epoxide addition has ended, there preferably follows a period of further reaction for completion of the conversion. The further reaction can be conducted, for example, by continued reaction under reaction conditions (i.e. maintenance, for example, of the temperature and the pressure) without addition of reactants.

Preferably, the further reaction is effected with mixing of the reaction mixture, especially with stirring.

The DMC catalyst typically remains in the reaction mixture or in the chlorinated alkoxylation products of the first step (i).

Unreacted epoxides and any further volatile constituents can be removed directly at the end of the first step (i) or else after the second step (ii) in the optional third step (iii), for example by vacuum distillation, steam or gas stripping, or other methods of deodorization.

The reaction products of the first step (i) of the process according to the invention feature monomer units of the [—$CH_2$—CH($CH_2$Cl)—O—] type. The reaction products of the process are preferably compounds of the formula (III)

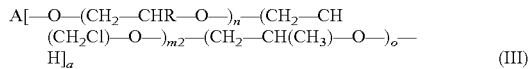

$$A[\text{—O—}(CH_2\text{—CHR—O—})_n\text{—}(CH_2\text{—CH}(CH_2Cl)\text{—O—})_{m_2}\text{—}(CH_2\text{—CH}(CH_3)\text{—O—})_o\text{—}H]_a \qquad (III)$$

where
A, R, n, o and a are each as defined above and
$m_2$ is 1 to 50, preferably greater than 1 up to 30, more preferably 2 up to 20.

The alkoxylation products of the first step (i) have one or more chemically bonded chlorine atoms, preferably from 2 to 50, more preferably from 2 to 40 and most preferably from 3 to 25 chlorine atoms.

The weight-average molar mass of the alkoxylation products of the first step (i) is preferably from 200 to 50 000 g/mol, more preferably 800 to 35 000 g/mol, especially preferably 1000 to 25 000 g/mol.

Particularly preferred alkoxylation products of the first step (i) of the process according to the invention have 3 to 25 chlorine atoms and have a weight-average molar mass of 1200 to 25 000 g/mol.

Products of high molar mass that are rich in units chemically incorporated from ethylene oxide and/or epichlorohydrin after ring opening have a tendency to crystallize in the course of cooling and may be opaque.

Quantitative analysis of the chlorine content in the alkoxylation product can be effected, for example, with the aid of $^{13}$C NMR spectroscopy.

GPC measurements allow the determination of the polydispersity and mean molar masses.

Reactors used for the alkoxylation in the first process step may in principle be any suitable reactor types that allow control over the reaction and its exothermicity. The first process step can be effected continuously, semi-continuously or else batchwise, in a manner known in process technology. As well as stirred tank reactors, it is also possible to use jet loop reactors with a gas phase and external heat exchangers, as described, for example, in EP-A-0 419 419, or internal heat exchanger tubes as described in WO 01/62826. In addition, it is possible to use gas phase-free loop reactors.

The chlorinated alkoxylation products of the first step (i) contain monomer units of the [—$CH_2$—CH($CH_2$Cl)—O—] type and, according to the molar mass, are of low to high viscosity or even solid.

Preferably, the process according to the invention is executed in the first step (i) in such a way that propylene oxide or ethylene oxide is metered in as the last monomer.

It is thus a feature of the intermediates of the process that they have an oxypropylene group or oxyethylene group in a terminal position.

Second Step (ii):

The reaction conditions of the second step (ii) of the process according to the invention, for example temperature, use of solvent, starting amount of carboxylate, reaction time, affect the reaction rate and the conversion in the substitution reaction.

The use of a molar deficiency of carboxylate based on the Cl-containing units referred to by index $m_2$ results in reaction products having a residual content of Cl-containing repeat units. When a molar excess of carboxylate is used, based on the units referred to by index $m_2$, the crude product contains excess carboxylate which can optionally be removed by filtration.

The alkoxylation products obtained in the first step (i), especially the compounds of formula (III) containing chlorine in chemically bonded form, in the process according to the invention, are converted in the second step (ii) by a reaction with one or more carboxylate compounds, with elimination of the chlorine bonded to the carbon and with formation of the corresponding pendant acyloxy groups, to the inventive polyoxyalkylenes having pendant long-chain acyloxy radicals, for example the compounds of the formula (I).

The acyloxy radicals in the inventive polyoxyalkylenes are radicals of organic acids present in their anionic form as carboxylate at least with one or more metallic counterions or/and as ammonium salts.

Carboxylates in the context of this invention refer to those compounds having at least one COO$^-$ group bonded to an organic radical. Suitable carboxylates are in principle all carboxylate compounds, preferably alkali metal, ammonium and alkaline earth metal carboxylates, more preferably sodium carboxylates and potassium carboxylates.

The organic radical bonded to the carboxylate group is a linear or branched, saturated or unsaturated aliphatic hydrocarbyl radical or an aromatic hydrocarbyl radical having 6 to 21 carbon atoms, preferably having 6 to 17 carbon atoms.

Preferred carboxylates are the salts of aliphatic carboxylic acids having 7 to 18 carbon atoms, for example the carboxylates of 2-ethylhexanoic acid, isotridecylcarboxylic acid, capric acid, lauric acid, myristic acid, palmitic acid, stearic acid, oleic acid, linoleic acid, linolenic acid, isostearic acid, ricinoleic acid, undecylenoic acid and mixtures thereof. These also include the fatty acid mixtures of native origin, obtained, for instance, from palm oil, coconut oil, olive oil, rapeseed oil, soya oil, sunflower oil, safflower oil, linseed oil, peanut oil, castor oil, tall oil. Likewise suitable are the sodium and potassium salts of the mixtures that have arisen through dimerization and trimerization of unsaturated fatty acids and contain an average of more than one carboxyl group per molecule.

Further-preferred carboxylates are the sodium and potassium salts of aromatic carboxylic acids having 7 to 22 carbon atoms, for example benzoic acid, naphthalenecarboxylic acid, salicylic acid.

Very particularly preferred carboxylates are the salts of liquid carboxylic acids such as oleic acid, linoleic acid, 2-ethylhexanoic acid, isostearic acid, isotridecylcarboxylic acid and the salts of liquid fatty acid mixtures.

Especially preferred carboxylates are the sodium and potassium salts of the liquid carboxylic acids and liquid fatty acid mixtures, and mixtures of said salts.

Carboxylates usable in the second step (ii) of the process according to the invention and mixtures thereof may, as appropriate, be used in solid form or as aqueous solutions or dispersions. Suitable solvents and dispersants are, for example, alcohols such as ethanol or methanol. The concentration of the solutions can be selected freely in principle, but is guided by the solubility of the carboxylate in the particular solvent. 10 to 80 per cent by weight solutions are preferable.

It may be advantageous to conduct the second step (ii) of the process according to the invention under inert conditions, for example a protective gas, for example nitrogen or argon. Under protective gas, for example, side reactions such as oxidations are avoided. The products which have been prepared under protective gas may be free of dark discolouration.

It may be advantageous to generate the particular carboxylate in the reaction vessel in situ from the carboxylic acid in question and the alkali metal or alkaline earth metal hydroxides, with the possibility of using solvents such as water and/or alcohols, for example ethanol and methanol, and mixtures of solvents.

The amount of the carboxylate used is guided by the chlorine content of the product of the first process step (i) and may be substoichiometric, stoichiometric or else superstoichiometric in relation to Cl. For a preferred rapid and quantitative conversion, it is advantageous to use the carboxylate in a stoichiometric amount or in a molar excess based on the chlorine bound in the alkoxylation product.

Preference is given to using, for every 1 mol of chlorine, preferably 0.5 to 10 mol of carboxylate, more preferably 0.8 mol to 4 mol of carboxylate, especially preferably 0.9 mol to 2 mol of carboxylate, especially 0.95 mol to 1.3 mol of carboxylate.

By addition of comparatively small amounts of carboxylate, by premature termination of the reaction or by the choice of low temperatures of, for example, <140° C. in the second step (ii), it is possible to produce alkoxylation products or polyethers of formula (I) in which the chlorine has been only partially eliminated. In that case, $m_3$ in formula (I) is greater than 0.

The second step (ii) of the process according to the invention can be conducted with or without solvent. Suitable solvents are especially polar or protic compounds or the mixtures thereof which have been matched to the solubility of the polyether and the miscibility with the carboxylate. Preferred solvents are water or organic solvents such as dimethyl sulphoxide, ketones, for example acetone, methyl ethyl ketone and methyl isobutyl ketone, or ethers, for example tetrahydrofuran, or alcohols, for example methanol, ethanol, isopropanol, n-propanol, butanol, ethylene glycol, dipropylene glycol; the use of water as solvent is likewise possible. The reaction mixture may be present therein either in dissolved or dispersed form. The proportion of solvent in the mixture with the alkoxylation product in the second step (ii) is preferably 5% to 80% by weight, preferably 10% to 60% by weight, based on the overall mixture.

When water is used as solvent in the second step (ii) of the process according to the invention, it may be advantageous to add phase transfer catalysts. In some cases, this accelerates the reaction. Suitable phase transfer catalysts are known to those skilled in the art. Preferred phase transfer catalysts are, for example, quaternary ammonium and phosphonium compounds.

The second step (ii) of the process according to the invention is conducted at a temperature of 60° C. to 300° C., preferably of 80° C. to 250° C., more preferably at 120° C. to 220° C.

The process according to the invention has the advantage that the choice of temperature in the second step (ii) has a crucial influence on the degree of substitution. The degree of substitution is understood to mean the molar ratio of acyloxy groups in the end product to the chlorine content of the intermediate prior to execution of the second step (ii). For instance, it is possible, in the case of equimolar use of carboxylates in relation to the chlorine content, at temperatures exceeding 140° C. within the temperature range of the process, to achieve a degree of substitution of 0.95, 0.96, 0.97, 0.98, 0.99 to 1. Degrees of substitution greater than or equal to 0.95 mean full conversion if, at the same time, no chlorine can be detected any longer in the product mixture. At lower temperatures, a lower degree of substitution is achieved.

When solvents are used, the reaction can be conducted at the reflux temperature of the boiling solvent. It is preferable to increase the reaction temperature during the conversion and in doing so to remove the solvent by distillation. Preference is given to increasing the temperature up to 120° C. to 300° C. Particular preference is given, on increasing the temperature, to removing the solvent to an extent of more than 95%, 96%, 97%, 98%, especially more than 99%. Complete removal of the solvent is ascertained by methods familiar to those skilled in the art; for example, the water content can be determined according to Karl Fischer.

The reactants may be added in any sequence in the second step (ii) of the process according to the invention. It is possible either to initially charge the chlorinated alkoxylation products in the reaction vessel and to add the particular carboxylate or the mixture of carboxylic acid and metal hydroxide while stirring or, conversely, to initially charge the carboxylate or the mixture of carboxylic acid and metal hydroxide and then to add the epichlorohydrin polyether or the epichlorohydrin alkoxylation product. Solvents may, as appropriate, be initially charged or else fed in together with the second reactant or else separately.

The addition of the second reactant may be accomplished either continuously in a feed process or else in portions.

If an organic solvent or water is used, it can be initially charged in the reactor together with the first reaction component. Alternatively, the solvent may also be fed in continuously or batchwise together with the second reaction component. In this case, it is favourable to add the second reactant in dissolved form. The second reactant can be added within a few minutes or else gradually, for example over several hours. A subsequent stirring period (further reaction period) of sufficient length can ensure that the chlorine substitution runs to completion. The duration of the further reaction can be determined by simple preliminary tests. Preferably, the addition and further reaction last for about 2 h to 8 h in total.

In the course of the reaction in step (ii) of the process according to the invention, the chloride of the particular metal of the carboxylate used is formed. The metal chlorides, for example NaCl or KCl, are only partly soluble in the reaction mixture and partly precipitate out as solids.

In a preferred embodiment of the process according to the invention, the carboxylate is produced in situ. For this purpose, the carboxylic acid is combined with the solution of the metal hydroxide, preferably NaOH or KOH as aqueous alkali or as alcoholic solution. Optionally, water or the organic solvent can be removed by distillation. The chlorinated polyether is subsequently added continuously or in portions over a period of 30 min to 2 h while stirring. A preferred reaction temperature is 150° C. to 220° C., more preferably 180° C. to 210° C. After a further reaction time of about 4 h, full conversion has usually been achieved. The analysis for ester content and for residual chlorine bonded to the polyether or alkoxylation product can be conducted by means of $^{13}$C NMR analysis.

The product obtained in the second step (ii) of the process according to the invention is a reaction mixture (a composition) including the inventive polyoxyalkylene having pendant long-chain acyloxy radicals, preferably the polyoxyalkylenes of the formula (I).

Noninventive example B9 shows that the reaction in the second step (ii) does not work with short-chain carboxylates. No exchange of the chlorine atoms takes place. In the product, no corresponding short-chain acyloxy radicals were detectable with the aid of $^{13}$C NMR spectroscopy.

Optional Third Step (iii): In order to neutralize any carboxylate excess after the reaction in the second step (ii) has ended, it is possible to use any acids in principle. Preferably, suitable acids are carboxylic acids such as lactic acid and aqueous mineral acids, a preferred mineral acid being phosphoric acid.

Preference is given to adding a sufficient amount of acid to establish an approximately neutral pH of 6 to 8 in the reaction mixture. The neutralization may, as appropriate, be conducted before or after any solvent or water distillation conducted.

There are several ways of removing chloride salts from the reaction mixture. For instance, the substantially anhydrous reaction mixture from the second step (ii), optionally dissolved in a solvent, can be freed of salts by filtration.

If required, a portion of salt may already have been removed beforehand by means of a phase separation. For this purpose, the reaction mixture from the second step (ii) is admixed with water and stirred in order to dissolve undissolved chloride. The brine that arises is separated from the organic phase after a certain settling time. The organic phase still contaminated with residual salt can subsequently, for example, be distilled to free it of water or filtered.

The most favourable mode of workup in the third step (iii) is guided in each case by the available apparatus options and technical possibilities and by the specific properties of the polyoxyalkylene having pendant long-chain acyloxy radicals, such as the hydrophilicity, density, viscosity and/or solubility thereof.

The inventive polyoxyalkylenes having pendant long-chain acyloxy radicals, especially those of the formula (I), can be used as precursors for a further chemical conversion or directly for preparation of compositions comprising these polyoxyalkylenes.

By the process according to the invention, it is possible to prepare the likewise inventive compositions comprising the alkoxylation products of the formula (I) and mixtures thereof.

The examples adduced below illustrate the present invention by way of example, without any intention of restricting the invention, the scope of application of which is apparent from the entirety of the description and the claims, to the embodiments specified in the examples.

The inventive polyoxyalkylenes having pendant long-chain acyloxy radicals, the process for preparation thereof and the inventive use are described hereinafter by way of example, without any intention that the invention should be restricted to these illustrative embodiments. Where ranges, general formulae or compound classes are specified hereinbelow, these shall include not just the corresponding ranges or groups of compounds that are explicitly mentioned but also all sub-ranges and sub-groups of compounds which can be obtained by extracting individual values (ranges) or compounds. Where documents are cited in the context of the present description, it is intended that their content shall form a full part of the disclosure-content of the present invention. Where percentages are given below, they are percentages in % by weight unless stated otherwise. In the case of compositions, the percentages, unless stated otherwise, are based on the overall composition. Where average values are reported below, the averages in question are mass averages (weight averages), unless otherwise indicated. Where measurement values are reported below, these measurement values, unless stated otherwise, have been determined under a pressure of 101 325 Pa and at a temperature of 25° C.

The inventive polyoxyalkylenes having pendant long-chain acyloxy radicals are usable in various ways, preferably as interface-active polymers such as surfactants, emulsifiers, antifoams, deaerating agents, wetting agents, dispersants, detergents, paint levelling agents, lubricants, as cosmetic additives and as foam stabilizers, especially in polyurethane foam.

The inventive compounds of the formula (I) can be used as chemical precursors for a multitude of possible chemical reactions.

Inventive compounds of formula (I) having C-C double bonds such as allyl or 1-hexenyl groups open up a route to SiC-bonded polyether siloxane copolymers with addition of siloxanes having SiH groups onto unsaturated polyethers. The multitude of documents includes EP 1 520 870, EP 0 075 703, U.S. Pat. No. 3,775,452 and EP 1 031 603. Usually transition metal-catalysed addition gives rise to polyether siloxanes which themselves can likewise be used as interface-active active polymers such as surfactants, emulsifiers, antifoams, deaerating agents, wetting agents, dispersants, detergents, paint levelling agents, lubricants, as cosmetic additives and as foam stabilizers, especially in polyurethane foam.

Suitable catalysts for the hydrosilylation reaction are, for example, transition metal catalysts of the d elements of transition groups 8 to 10 of the Periodic Table of the Elements, especially platinum compounds, for example hexachloroplatinic acid, cis-platin, bis(cyclooctene)platinum dichloride, carbo-platin, platinum(0) divinyltetramethyldisiloxane complexes, what are called Karstedt catalysts, or else platinum(0) complexes complexed with different olefins. Additionally suitable in principle are rhodium, iridium and ruthenium compounds, for example tris(triphenylphosphine)rhodium(I) chloride or tris(triphenylphosphine)ruthenium(II) dichloride. Catalysts preferred in the context of the process according to the invention are platinum(0) complexes; especially preferred are optionally modified Karstedt catalysts which are prepared, for example, according to EP-A-1 520 870.

EXAMPLES

GPC Measurements:

GPC measurements for determining the polydispersity and mean molar masses Mw were conducted under the following measurement conditions: SDV 1000/10 000 A column combination (length 65 cm), temperature 30° C., THF as mobile phase, flow rate 1 ml/min, sample concentration 10 g/l, RI detector, evaluation against polypropylene glycol standard.

Determination of the Content of Chlorine and Vinyl Groups:

The determination of the content of chlorine and vinyl groups was conducted with the aid of $^{13}$C NMR spectroscopy. An NMR spectrometer of the Bruker Avance 400 type was used. For this purpose, the samples were dissolved in $CDCl_3$.

Determination of OH Number:

Hydroxyl numbers were determined according to the method DGF C-V 17 a (53) of the Deutsche Gesellschaft fur Fettwissenschaft [German Society for Fat Science]. This involved acetylating the samples with acetic anhydride in the presence of pyridine and determining the consumption of acetic anhydride by titration with 0.5 n potassium hydroxide solution in ethanol using phenolphthalein.

The iodine numbers [g of iodine/100 g of sample] are determined by the method according to Hanus, known as method DGF C-V 11 a (53) of the Deutsche Gesellschaft fur Fette.

Example 1

Synthesis Examples

Example A

Preparation of Epichlorohydrin Alkoxylation Products

Example A1

Precursor 1

A 3 liter autoclave was initially charged with 339.6 g of poly(oxypropylene) monobutyl ether as starter (mass-average molar mass $M_w$=382 g/mol) and 2.25 g of zinc hexacyanocobaltate DMC catalyst and heated to 130° C. while stirring. The reactor was evacuated down to an internal pressure of 30 mbar in order to remove any volatile ingredients present by distillation. To activate the DMC catalyst, a portion of 80 g of propylene oxide was fed in. After the reaction had commenced and the internal pressure had dropped, firstly a further 179 g of propylene oxide were metered in while cooling. Subsequently, under the same conditions, 1645 g of propylene oxide and 494 g of epichlorohydrin in a mixture were metered in at 130° C. and a maximum internal reactor pressure of 1.5 bar within 2 h. This was followed by further reaction at 130° C. for 30 minutes, in the course of which the internal reactor pressure dropped to 0.5 bar. Finally, as end block, a further 259 g of propylene oxide were added on at 130° C. Another period of continued reaction under the same conditions was followed by a degassing stage. In the course of this, volatile components such as residual propylene oxide and epichlorohydrin were distilled off under reduced pressure at 130° C. The virtually colourless chlorinated alkoxylation product of low viscosity was cooled to below 90° C. and discharged from the reactor. By GPC the product had a weight-average molar mass of 2700 g/mol and a polydispersity $M_w/M_n$ of 1.37, and by $^{13}$C NMR analysis contained 5.7 mol of Cl per molecule.

Example A2

Precursor 2

A 3 liter autoclave was initially charged with 615.6 g of poly(oxypropylene-co-oxyethylene) monoallyl ether as starter (mass-average molar mass $M_w$=780 g/mol, 20% by weight of oxyethylene units, 80% by weight of oxypropylene units) and 2.05 g of zinc hexacyanocobaltate DMC catalyst and heated to 130° C. while stirring. The reactor was evacuated down to an internal pressure of 30 mbar in order to remove any volatile ingredients present by distillation. To activate the DMC catalyst, a portion of 75 g of propylene oxide was fed in. After the reaction had commenced and the internal pressure had dropped, firstly a further 155 g of propylene oxide were metered in while cooling. Subsequently, under the same conditions, 1469 g of propylene oxide and 439 g of epichlorohydrin in a mixture were metered in at 130° C. and a maximum internal reactor pressure of 1.5 bar within 135 min. This was followed by further reaction at 130° C. for 30 minutes. Finally, as end block, a further 230 g of propylene oxide were added on at 130° C. Another period of continued reaction was followed by a degassing stage under reduced pressure at 130° C. The virtually colourless chlorinated alkoxylation product of low viscosity was cooled to below 90° C. and discharged from the reactor. By GPC the product had a weight-average molar mass of 2754 g/mol and a polydispersity $M_w/M_n$ of 1.28, and by $^{13}$C NMR analysis contained 6.0 mol of Cl per molecule. The iodine number was 6.9 g of iodine/100 g.

Example A3

Precursor 3

A 3 liter autoclave was initially charged with 425.1 g of poly(oxypropylene-co-oxyethylene) monobutyl ether as starter (mass-average molar mass $M_w$=540 g/mol, 60% by weight of oxyethylene units, 40% by weight of oxypropylene units) and 2.15 g of zinc hexacyanocobaltate DMC catalyst and heated to 130° C. while stirring. The reactor was evacuated down to an internal pressure of 30 mbar in order to remove any volatile ingredients present by distillation. To activate the DMC catalyst, a portion of 93 g of propylene oxide was fed in. After the reaction had commenced and the internal pressure had dropped, while cooling and at internal temperature 130° C., 930 g of propylene oxide, 1059 g of ethylene oxide and 222 g of epichlorohydrin in a mixture were metered in at a maximum internal reactor pressure of 1.3 bar within 3.5 h. A 30-minute post-reaction at 130° C. followed. Finally, as end block, a further 353 g of ethylene oxide were added at 130° C. Another period of continued reaction was followed by a degassing stage under reduced pressure at 130° C. The virtually colourless chlorinated alkoxylation product of low viscosity was cooled to below 90° C. and discharged from the reactor. By $^{13}$C NMR analysis, the product contained 3.0 mol of Cl per molecule.

Example A4

Precursor 4

A 3 liter autoclave was initially charged with 392.4 g of poly(oxypropylene-co-oxyethylene) monobutyl ether as starter (mass-average molar mass $M_w$=540 g/mol, 60% by weight of oxyethylene units, 40% by weight of oxypropylene units) and 2.23 g of zinc hexacyanocobaltate DMC catalyst and heated to 130° C. while stirring. The reactor was evacuated down to an internal pressure of 30 mbar in order to remove any volatile ingredients present by distillation. To activate the DMC catalyst, a portion of 90 g of propylene oxide was fed in. After the reaction had commenced and the internal pressure had dropped, while cooling and at internal temperature 130° C., 837 g of propylene oxide, 953 g of ethylene oxide and 400 g of epichlorohydrin in a mixture were metered in at a maximum internal reactor pressure of 1.3 bar within 3.5 h. A 30-minute post-reaction at 130° C. followed. Finally, as end block, a further 318 g of ethylene oxide were added at 130° C. Another period of continued reaction was followed by a degassing stage under reduced pressure at 130° C. The virtually colourless chlorinated alkoxylation product of low viscosity was cooled to below 90° C. and discharged from the reactor. By $^{13}$C NMR analysis, the product contained 6.0 mol of Cl per molecule.

Example B

Preparation of the Inventive Ester-Modified Alkoxylation Products

Example B1

A glass flask equipped with a stirrer and distillation apparatus was inertized with nitrogen, then initially charged with 300.0 g of precursor 1 and heated to 80° C. Within 20 min, 143.0 g of solid potassium laurate were added in portions while stirring. The resultant suspension was heated up to 120° C. and stirred at 120° C. and about 20 mbar with distillative removal of volatiles for 3 h. The reaction product was cooled down to 80° C. and salts were removed by filtration. The liquid reaction product was yellowish and slightly cloudy and, according to the $^{13}$C NMR spectrum, had an average of 1.05 pendant lauric ester groups per molecule and still had 4.7 mol of organically bound chlorine.

Example B2

The experiment described in B1 was repeated, except that, after a reaction time of 3 h at 120° C., the reaction temperature was increased to 180° C. After 1 further hour of reaction time, the reaction mixture was cooled as described above and filtered. The liquid reaction product was yellowish and slightly cloudy and, according to the $^{13}$C NMR spectrum, had an average of 2.9 pendant lauric ester groups per molecule and still had 2.8 mol of organically bound chlorine.

Example B3

A glass flask equipped with a stirrer and distillation apparatus was inertized with nitrogen, then initially charged with 300.0 g of precursor 1 and heated to 80° C. Within 15 min, 176.7 g of solid potassium palmitate were added in portions while stirring. The resultant suspension was heated up to 180° C. and stirred at 180° C. and about 20 mbar with distillative removal of volatiles for 4 h. The reaction product was cooled down to 80° C. and salts were removed by filtration. The liquid reaction product was yellowish and slightly cloudy and, according to the $^{13}$C NMR spectrum, had an average of 3.0 pendant palmitic ester groups per molecule and still had 2.7 mol of organically bound chlorine.

Example B4

A glass flask equipped with a stirrer and distillation apparatus was inertized with nitrogen, then initially charged with 300.0 g of precursor 1 and heated to 80° C. Within 15 min, 192.2 g of solid potassium oleate were added in portions while stirring. The resultant mixture was heated up to 200° C. and stirred at 200° C. and about 20 mbar with distillative removal of volatiles for 4 h. The reaction product was cooled down to 80° C. and salts were removed by filtration. The liquid reaction product was brownish and slightly cloudy and, according to the $^{13}$C NMR spectrum, had an average of 4.9 pendant oleic ester groups per molecule and still had 0.8 mol of organically bound chlorine.

Example B5

A glass flask equipped with a stirrer and distillation apparatus was inertized with nitrogen, then initially charged with 211.1 g of oleic acid. 308 g of a 20% by weight ethanolic KOH solution were added while stirring. At 50° C., 300.0 g of precursor 1 were metered in within 10 min and the mixture was heated to 200° C. with distillative removal of ethanol. With further distillative removal of volatiles at about 20 mbar, the mixture was stirred at 200° C. for 4 h. The reaction product was cooled down to 80° C. and salts were removed by filtration. The liquid reaction product was brownish and slightly cloudy and, according to the $^{13}$C NMR spectrum, had an average of 5.7 pendant oleic ester groups per molecule and no longer had any organically bound chlorine.

Example B6

A glass flask equipped with a stirrer and distillation apparatus was inertized with nitrogen, then initially charged with 85.0 g of oleic acid. 84.4 g of a 20% by weight ethanolic KOH solution were added while stirring. At 50° C., 308.4 g of precursor 3 were metered in within 10 min and the mixture was heated to 200° C. with distillative removal of ethanol. With further distillative removal of volatiles at about 20 mbar, the mixture was stirred at 200° C. for 4 h. The reaction product was cooled down to 80° C. and salts were removed by filtration. The waxy reaction product was brownish and slightly cloudy and, according to the $^{13}$C NMR spectrum, had an average of 3 pendant oleic ester groups per molecule and no longer had any organically bound chlorine.

Example B7

A glass flask equipped with a stirrer and distillation apparatus was inertized with nitrogen, then initially charged with 169.7 g of oleic acid. 186.3 g of a 20% by weight ethanolic KOH solution were added while stirring. At 50° C., 300.0 g of precursor 4 were metered in within 10 min and the mixture was heated to 200° C. with distillative removal of ethanol. With further distillative removal of volatiles at about 20 mbar, the mixture was stirred at 200° C. for 4 h. The reaction product was cooled down to 80° C. and salts were removed by filtration. The liquid reaction product was brownish and slightly cloudy and, according to the $^{13}$C NMR spectrum, had an average of 6 pendant oleic ester groups per molecule and no longer had any organically bound chlorine.

Example B8

A glass flask equipped with a stirrer and distillation apparatus was inertized with nitrogen, then initially charged with 169.5 g of oleic acid. 186.2 g of a 20% by weight ethanolic KOH solution were added while stirring. At 50° C., 298.5 g of precursor 2 were metered in within 10 min and the mixture was heated to 200° C. with distillative removal of ethanol. With further distillative removal of volatiles at about 20 mbar, the mixture was stirred at 200° C. for 4 h.

The reaction product was cooled down to 80° C. and salts were removed by filtration. The liquid reaction product was brownish and slightly cloudy and, according to the $^{13}C$ NMR spectrum, had an average of 5.7 pendant oleic ester groups per molecule and had 0.3 mol of organically bound chlorine.

Example B9

(Non-Inventive)

A glass flask equipped with a stirrer and distillation apparatus was inertized with nitrogen, then initially charged with 300.0 g of precursor 1 and heated to 80° C. Within 15 min, 49.3 g of solid sodium acetate were added in portions while stirring. The resultant suspension was heated up to 180° C. and stirred at 180° C. and about 20 mbar with distillative removal of volatiles for 4 h. The reaction mixture was cooled down to 80° C. and comparatively large amounts of salt were removed by filtration. The liquid reaction product was yellowish and, according to the $^{13}C$ NMR spectrum, did not have any pendant ester groups, and instead still had 6 mol of organically bound chlorine. No reaction in the sense of the invention took place.

Example C

Hydrosilylating Linkage of Unsaturated Polyethers Bearing Inventive Acyloxy Radicals to SiH Siloxanes Example C1

A linear polydimethylsiloxane having an average of 32 Si units and terminal SiH functionalization and the precursor from Example B8 were heated to 50° C. while stirring in a four-neck flask equipped with a precision glass stirrer, an internal thermometer and a reflux condenser. The excess of allyl groups in the polyether over SiH groups in the siloxane here was 35 mol %. A total of 30 ppm of platinum in the form of a platinum(0) catalyst modified according to EP 1520870 were metered in portions with a syringe within 8.5 h. During the reaction, the temperature was increased first to 70° C., then to 100° C. The conversion determined by gas volumetric means was quantitative after 20 hours. The polyether siloxane obtained was cloudy.

Example C2

A linear polydimethylsiloxane having an average of 35 Si units and a mean number of 5 —O—Si(CH$_3$)H— units in the chain and the precursor from Example B8 were heated to 50° C. while stirring in a four-neck flask equipped with a precision glass stirrer, an internal thermometer and a reflux condenser. The excess of allyl groups in the polyether over SiH groups in the siloxane here was 35 mol %. A total of 40 ppm of platinum in the form of a platinum(0) catalyst modified according to EP 1520870 were metered in portions with a syringe within 8.5 h. During the reaction, the temperature was increased to 70° C. The conversion determined by gas volumetric means was quantitative after 14 hours. The polyether siloxane obtained was cloudy.

The invention claimed is:

1. A polyoxyalkylene of formula (I)

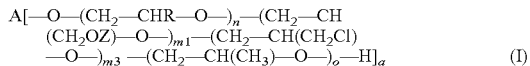

where

A is hydrogen or an organic radical derived from an organic starter compound selected from the group consisting of monohydric monomeric alcohols, polyhydric monomeric alcohols, oligomeric alcohols, and polymeric alcohols, R is independently hydrogen, an alkyl group comprising 2-18 carbon atoms or a phenyl radical, Z is a radical of an organic acid of formula —C(=O)—Z$_E$ where Z$_E$ is an organic radical selected from the group consisting of linear or branched, saturated or unsaturated aliphatic hydrocarbyl radicals having 7 to 22 carbon atoms or aromatic hydrocarbyl radicals having 6 to 21 carbon atoms, m$_1$ is a number of 1 to 50, m$_3$ is 0, n is a number of 0 to 200, o is a number of 1 to 1000, and a is a number of 1 to 8;

wherein the polyoxyalkylene does not comprise a terminal structural unit comprising an acyloxy radical;

wherein the polyoxyalkylene does not include a methylidene group;

where the polyoxyalkylene does not comprise a halogen atom.

2. The polyoxyalkylene according to claim 1, which has a weight-average molar mass of 400 to 50 000 g/mol.

3. An interface-active polymer, comprising the polyoxyalkylenes according to claim 1.

4. A surfactant, comprising the interface-active polymer according to claim 3.

5. The polyoxyalkylene according to claim 1, where Z$_E$ is an organic radical selected from the group consisting of linear or branched, saturated or unsaturated aliphatic hydrocarbyl radicals having 7 to 22 carbon atoms or aromatic hydrocarbyl radicals having 6 to 17 carbon atoms.

6. The polyoxyalkylene according to claim 1, where —C(=O)—Z is selected from the group consisting of carboxylates of 2-ethylhexanoic acid, isotridecylcarboxylic acid, capric acid, lauric acid, myristic acid, palmitic acid, stearic acid, oleic acid, linoleic acid, linolenic acid, isostearic acid, ricinoleic acid, undecylenoic acid and mixtures thereof.

7. The polyoxyalkylene according to claim 1, where —C(=O)—Z is selected from the group consisting of carboxylates of fatty acid mixtures obtained from palm oil, coconut oil, olive oil, rapeseed oil, soya oil, sunflower oil, safflower oil, linseed oil, peanut oil, castor oil, and tall oil.

8. The polyoxyalkylene according to claim 1, wherein A has a weight-average molar mass of 15 to 4983 g/mol.

* * * * *